(12) United States Patent
De Vos

(10) Patent No.: US 8,097,736 B2
(45) Date of Patent: Jan. 17, 2012

(54) STABLE LACTIDE PARTICLES

(75) Inventor: Sicco De Vos, Arnhem (NL)

(73) Assignee: Purac Biochem B.V., Gorinchem (NL)

( * ) Notice: Subject to any disclaimer, the term of this patent is extended or adjusted under 35 U.S.C. 154(b) by 12 days.

(21) Appl. No.: 11/987,256

(22) Filed: Nov. 28, 2007

(65) Prior Publication Data

US 2008/0132715 A1 Jun. 5, 2008

Related U.S. Application Data

(63) Continuation of application No. 11/878,723, filed on Jul. 26, 2007, now abandoned.

(60) Provisional application No. 60/861,725, filed on Nov. 30, 2006.

(30) Foreign Application Priority Data

Nov. 28, 2006 (EP) .................................. 06124934
Jul. 26, 2007 (EP) .................................. 07113211

(51) Int. Cl.
*C07D 319/12* (2006.01)
(52) U.S. Cl. ........ 549/274; 426/133; 426/268; 426/654; 528/354; 528/357; 525/415
(58) Field of Classification Search .................. 549/274; 426/329, 654, 274, 133
See application file for complete search history.

(56) References Cited

U.S. PATENT DOCUMENTS

| 1,995,970 | A | | 3/1935 | Dorough et al. |
| 5,053,485 | A | | 10/1991 | Nieuwenhuis et al. |
| 5,264,592 | A | * | 11/1993 | Fridman et al. ............... 549/274 |
| 5,646,238 | A | * | 7/1997 | Ikeda et al. ................... 528/361 |
| 5,801,255 | A | * | 9/1998 | Ohara et al. ................... 549/274 |
| 6,310,218 | B1 | * | 10/2001 | O'Brien et al. ............... 549/231 |
| 6,313,319 | B1 | * | 11/2001 | Ohara et al. ................... 549/274 |
| 6,875,839 | B2 | | 4/2005 | Gerking et al. |

FOREIGN PATENT DOCUMENTS

| EP | 1 310 517 A1 | 5/2003 |
| WO | WO 93/15127 A1 | 8/1993 |

OTHER PUBLICATIONS

Sarazin et al "Controlled preparation and properties of porous poly ( -lactide) obtained from a co-continuous blend of two biodegradable polymers", Biomaterials, vol. 25, Issue 28, 2004, pp. 5965-5978.*

* cited by examiner

Primary Examiner — James J Seidleck
Assistant Examiner — Gregory Listvoyb
(74) Attorney, Agent, or Firm — Oliff & Berridge, PLC

(57) ABSTRACT

The present invention is directed to a method for the manufacture of stable lactide particles, more specifically lactide particles which are stable enough to be stored and transported at room temperature and have a quality high enough for use as starting material for polylactic acid. The lactide particles are obtained via a flaking process, comprising the contacting of a continuous flow of molten lactide with a surface on which the lactide solidifies and subsequently is removed from said surface.

15 Claims, No Drawings

STABLE LACTIDE PARTICLES

This nonprovisional application claims the benefit of U.S. Provisional Application No. 60/861,725, filed Nov. 30, 2006 and is a Continuation-in-Part of application Ser. No. 11/878,723 filed Jul. 26, 2007. The disclosure of the prior applications is hereby incorporated by reference herein in its entirety.

The present invention relates to lactide particles, more specifically to lactide particles which are stable enough to be stored and transported at room temperature and which have a quality high enough for use as starting material for polylactic acid.

The continued depletion of landfill space, the depletion of the fossil energy reserves, in particular of oil, the subsequent need to use therefore and in relation to various greenhouse gas related issues, new carbon form renewable resources, and the problems associated with incineration of waste, have led to the need for development of truly biodegradable polymers to be utilized as substitutes for non-biodegradable or partially biodegradable, petrochemical-based polymers in packaging, paper coating and other non-medical industry applications, hereinafter referred to as bulk applications. The use of lactic acid and lactide to manufacture a biodegradable polymer is well known in the medical industry. As disclosed by Nieuwenhuis et al. (U.S. Pat. No. 5,053,485), such polymers have been used for making biodegradable sutures, clamps, bone plates and biologically active controlled release devices. It will be appreciated that processes developed for the manufacture of polymers to be utilized in the medical industry have incorporated techniques that respond to the need for high purity and biocompatibility in the final polymer product. Furthermore, the processes were designed to produce small volumes of high dollar-value products, with less emphasis on manufacturing cost and yield.

It is known that lactic acid undergoes a condensation reaction to form polylactic acid upon dehydration. Dorough recognized and disclosed in U.S. Pat. No. 1,995,970, that the resulting polylactic acid is limited to a low molecular weight polymer of limited value, based on physical properties, due to a competing depolymerization reaction in which the cyclic dimer of lactic acid, lactide, is generated. As the polylactic acid chain lengthens, the polymerization reaction rate decelerates until it reaches the rate of the depolymerization reaction, which effectively, limits the molecular weight of the resulting polycondensation polymers.

Therefore, in most publications, processes for the production for polylactic acid are described wherein from lactic acid first a prepolymer is prepared, said prepolymer is depolymerized in the presence of a catalyst to form crude lactide by a ring-closure reaction, said crude lactide is subsequently purified and lactide is used as starting material for the preparation of polylactic acid by ring-opening polymerization. For the purpose of this description the term polylactic acid and polylactide are used interchangeably. It is well known that lactic acid exists in two forms which are optical enantiomers, designated as D-lactic acid and L-lactic acid. Either D-lactic acid, L-lactic acid, or mixtures thereof may be polymerized to form an intermediate molecular weight polylactic acid which, after the ring-closure reaction, generates lactide as earlier disclosed. The lactide (sometimes also referred to as dilactide), or the cyclic dimer of lactic acid, may have one of three types of stereochemical configurations depending on whether it is derived from two L-lactic acid molecules, two D-lactic acid molecules or an L-lactic acid molecule and a D-lactic acid molecule. These three dimers are designated L-lactide, D-lactide, and meso-lactide, respectively. In addition, a 50/50 mixture of L-lactide and D-lactide with a melting point of about 126° C. is often referred to in the literature as D,L-lactide. The optical activity of either lactic acid or lactide is known to alter under certain conditions, with a tendency toward equilibrium at optical inactivity, where equal amounts of the D and L enantiomers are present. Relative concentrations of D and L enantiomers in the starting materials, the presence of impurities or catalysts, varying temperatures, residence times, and pressures are known to affect the rate of such racemization. The optical purity of the lactic acid or the lactide is decisive for the stereochemistry of the polylactic acid obtained upon ring-opening polymerization of the lactide. With respect to polylactic acid, stereochemistry, and molecular weight are the key parameters for polymer quality.

When preparing polylactic acid for the medical industry often crystalline powdery lactide is used as the starting material. These crystals, which are commercially available for over 30 years now, are highly hygroscopic and are packed under inert atmosphere in damp- and air-tight packages and stored in freezers (temperature below 12° C.). It will be clear that these precautions cannot be taken when polylactic acid is used for bulk applications because it would render the product too expensive.

In publications describing processes for the preparation of polylactic acid for bulk applications, the lactide formed and purified is directly fed in its molten, liquid form to a polymerization reactor to form polylactide. See for instance EP 0,623,153 and U.S. Pat. No. 6,875,839. By the direct conversion of the freshly prepared lactide to polylactic acid, the negative effects of the relative instability of lactide can be controlled by minimizing the residence time of the lactide in the reactor. However, this process requires that the lactide production and polylactic acid production are combined. This makes the process rather inflexible and creates an entrance barrier for new polylactic acid producers, because it requires large investments in equipment. Secondly, as the quality of the lactide is decisive for the molecular weight and stereochemistry that can be obtained in the polylactic acid, and the ring-closure process and purification require strict control of the temperature, pressure and residence time, it is also the most delicate part of the polylactic acid production process. The risk of failure in this part of the process enlarges the entrance barrier even more. If new polylactic acid producers for bulk applications could simply be provided with stable, high-quality lactide, this burden would be taken from them and substitution of petrochemical-based polymers with lactic acid-based (co)polymers could actually take place. It has been suggested to transport lactide in its molten form (melting point of D-lactide and L-lactide is 97° C.). Beside the fact that this type of transport is expensive, the transport and storage of lactide in molten state is also detrimental to the quality of the lactide because racemization, hydrolysis, and polymerization reactions are accelerated at these temperatures. The same problem occurs in the direct conversion process when the residence time of the lactide is not precisely controlled.

To this end the present invention is directed to a method for the manufacture of stable, high-quality lactide particles, said method comprising subjecting molten lactide to a flaking process that effectively transforms the liquid lactide melt to a coarse solid granulate. We have found that lactide particles, also referred to as flakes, produced via the flaking process according to the present invention are stable enough, in terms of chemically stable against occurrence of racemization, oxidation and hydrolysis, for storage and transport at ambient temperature and can readily be used as starting material for the production of polylactic acid for bulk applications. With stable lactide particles is meant that when storing the lactide particles having an initial free acid content of at most 5 meq/kg at 20 degrees Celsius in air, the free acid content will still be below 2000 after 10 weeks of storage.

Further, it was found that the flaking method or process according to the present invention is a rapid, cheap and surprisingly efficient method for producing stable lactide particles. The powdery crystalline lactides used in the medical industry are known to be manufactured via solvent crystallization as this is a technique with which the high chemical purity, that is required in medical applications, can be achieved. Solvent crystallization is however a very expensive, not environmentally friendly and a complex process due to the solvents that are used. The flaking process according to the present invention does not have these disadvantages.

The present flaking process does also not include lengthy processing times and additional extensive drying steps as is the case in for example when a prilling process is used to manufacture lactide particles. And further, problems such as racemization, hydrolysis and oxidation are prevented in using the flaking process according to the present invention, which therefore results in lactide particles of high quality, significantly higher than for example lactide particles made via prilling.

With the flaking process according to the present invention for example, a production rate could be obtained, depending on cooling temperature and drum rotational speed, which was minimally two to three times higher compared to an alternative process used for making lactide pastilles.

Furthermore, the resulting lactide flakes exhibit favorable properties making them very suitable for further processing. We found for example that the lactide flakes of the present invention can be relatively rapidly and easy processed further in a subsequent melting step leading to short residence times in this melting step. These short residence times offer the advantage that the risk of side reactions occurring, leading to for example the formation of lactic acid, lactoyllactic acid and water, is significantly reduced and thus the purity of the high quality lactide is preserved. In combination with the short residence times required, the temperature of the melting process can be lowered which also is positive as above-mentioned side reactions are less likely to occur. Further, the lactide particles made via the present flaking process are easy to disperse and thus less mechanical input is required for said homogenization process. This also reduces the risk of any side reactions occurring.

The lactide used in the flaking process according to the present invention is in the molten form, meaning that all lactide entering the solidification process is at a temperature above the melting point of the lactide. The flaking process comprises contacting a continuous flow of molten lactide with a surface with a temperature lower than the melting point of the lactide, allowing the lactide melt to solidify on said surface, and removing the solid lactide from that surface. Said surface may be cooled internally or externally and this can be done by various means as known to the skilled person.

In a preferred embodiment, the solidified lactide falls off of the surface under the influence of gravity and is thus removed from the surface.

In another preferred embodiment of the present invention, the solidified lactide on the surface is brought in contact with a means that removes or scrapes off the solidified lactide from said surface for product collection.

The apparatus used for the flaking process, or at least those parts that will be in contact with the lactide, preferably are prepared from corrosion-resistant material such as stainless steel. Further, to avoid water uptake of the lactide particles, the flaking process is preferably conducted under inert gas or dry atmosphere such as under nitrogen or dry air.

The flaking process according to the present invention may be performed with the conventional drum flaker apparatus used in the various thermal processes in chemical and food industries. With said drum flaker, molten lactide solidifies on the surface of the drum, after which it is removed from said surface either by means of gravity or by means of some type of scraping-device.

Various types of drum flakers are possible. Some examples hereof are rotating drum flakers wherein the rotating drum runs through a lactide melt in a dip pan underneath the drum, or rotating drum flakers wherein the lactide melt is "spread" over the rotating drum by means of for example an overhead applicator roll. It is of course also possible to apply the lactide melt on said rotating drum by other means well-known to the person skilled in the art. An example may be the spraying or dripping of lactide melt onto the surface of the drum.

Another example of a suited means for use in the flaking process is a belt flaker. Here the lactide melt can be applied on a cooled and moving belt instead of a rotating drum. The lactide solidifies after which it is removed either by means of gravity or by means of some type of scraping device.

Optionally a sieving step may be performed after the flaking process to avoid dusting during transport and during further processing to form polylactide.

Stable lactide particles can be made having a various surface area per unit of volume. Particles can be obtained with a surface area per unit of volume of between 1000 to 3000 $m^{-1}$ but also up to 10000 $m^{-1}$. It was found that lactide particles having a surface area per unit of volume of from 3000 to 10000 $m^{-1}$ showed the most ideal chemical stability for transport and storage and for further processing in the subsequent melting step or other processing steps.

As mentioned-above, the optical purity of the lactide is very important for the stereochemistry of the polylactic acid that is obtained. Therefore, it is preferred that the lactide present in the particles according to the invention contains more than 95% by weight D- or L-lactide, preferably more than 98.5% by weight D- or L-lactide, most preferably more than 99.5% D- or L-lactide by weight.

The water content of the lactide is also an important factor for the stability of the lactide particles. Contamination by water ultimately hydrolyzes the lactide to lactic acid. It was found that if the water content is below 200 ppm, the stability of the lactide particles when stored at ambient temperature in airtight and vapor-tight packages is ensured for several months. Preferably, the water content is below 100 ppm because it further increases the stability and thus shelf life of the lactide. The water content of the lactide can be measured by means of a Karl-Fisher titration as will be known by the artisan.

Also the free acid content of the lactide (either lactic acid or lactoyl lactic acid) is important for the stability and quality of the lactide. The presence of lactic acid and or lactoyl lactic acid in the lactide monomer will result in reduced rates of polymerization in the further manufacture of polylactic acid and in polylactic acid polymers of limited molecular weight. If the free acid content is below 50 milli-equivalents per Kg lactide (meq·$Kg^{-1}$) the stability of the lactide particles when stored at ambient temperature in air-tight and vapor-tight packages is ensured for several months. Preferably, the acid content is below 20 meq·$Kg^{-1}$ because it further increases the stability of the lactide. More preferably the acid content is between 0 and 10 meq·$Kg^{-1}$ and most preferably, the free acid content is less than 5 meq·$Kg^{-1}$. The free acid content can be measured by means of titration using for instance sodium methylate or potassium methylate in water-free methanol, as will be clear for the artisan. The lactide used as starting material for the shaping process may have been prepared by any conventional lactide process such as water removal from a lactic acid solution or condensation reaction of lactate esters, followed by a ring-closure reaction in a lactide reactor with the help of a catalyst. Optionally the crude lactide is further purified by for instance distillation and/or crystallization prior to the shaping process.

The lactide reactor can be of any suitable type that is designed for heat sensitive materials. A reactor that can maintain a uniform film thickness, such as a falling film or agitated thin-film evaporator is most preferred, because film formation increases the rate of mass transfer. When the rate of mass transfer is increased, lactide can quickly form and vaporize, and as lactide vaporizes, more lactide is produced as dictated by the polylactic acid/lactide equilibrium reaction. Optionally these lactide reactors are operated under reduced pressure such as between about 1 mmHg and 100 mmHg. The temperature of the lactide formation is kept between 150° C. and 250° C. Many suitable catalysts are known, such as metal oxides, metal halides, metal dusts, anionic clay, and organic metal compounds derived from carboxylic acids or the like. Normally a tin(II) catalyst is used for lactide formation.

Stabilizers may also be added to the lactide reactor in order to facilitate lactide formation and discourage degenerative lactic acid and lactide reactions. Stabilizers, such as antioxidants, either manufactured or naturally occurring, can be used to reduce the number of degradation reactions that occur during the process of polylactic acid and lactide production. Stabilizers may also reduce the rate of lactide formation during this process. Therefore, efficient production of lactide requires proper reactor design for minimal thermal severity and a proper balance between the catalyst and any use of process stabilizers.

A variety of stabilizers may be used. The stabilizing agent may include primary antioxidants and/or secondary antioxidants. Primary antioxidants are those which inhibit free radical propagation reactions, such as and not limited to alkylidene bisphenols, alkyl phenols, aromatic amines, aromatic nitro and nitroso compounds, and quinones. To prevent formation of free radicals secondary (or preventive) antioxidants break down hydroperoxides. Some non-limiting examples of secondary antioxidants include: phosphites, organic sulfides, thioethers, dithiocarbamates, and dithiophosphates. Antioxidants include such compounds as trialkyl phosphites, mixed alkyl/aryl phosphites, alkylated aryl phosphites, sterically hindered aryl phosphites, aliphatic spirocyclic phosphites, sterically hindered phenyl spirocyclics, sterically hindered bisphosphonites, hydroxyphenyl propionates, hydroxy benzyls, alkylidene bisphenols, alkyl phenols, aromatic amines, thioethers, hindered amines, hydroquinones, and mixtures thereof. Preferably, phosphite-containing compounds, hindered phenolic compounds, or other phenolic compounds are used as process stabilizing antioxidants. Most preferably, phosphite-containing compounds are used. The amount of process stabilizer used can vary depending upon the optical purity desired of the resulting lactide, the amount and type of catalyst used, and the conditions inside of the lactide reactor. Normally amounts varying from 0.01 to 0.3 wt. % process stabilizer can be used.

Next to stabilizers also dehydration or anti-hydrolysis agents may be used. These dehydration agents favor the formation of lactide. Further, they may be used in a later stage of the manufacturing process for polylactic acid as well as for preventing chain scission by water. Compounds based on peroxide may be used for this purpose but preferred are compounds containing the carbodiimide functionality. The carbodiimide compound is a compound having one or more carbodiimide groups in a molecule and also includes a polycarbodiimide compound. As a monocarbodiimide compound included in the carbodiimide compounds, dicyclohexyl carbodiimide, diisopropyl carbodiimide, dimethyl carbodiimide, diisobutyl carbodiimide, dioctyl carbodiimide, diphenyl carbodiimide, naphthyl carbodiimide, etc. may be exemplified. In particular industrially easily available compounds such as dicyclohexyl carbodiimide, diisopropyl carbodiimide or products like Stabaxol® by Rheinchemie are used.

It is also possible to add above-mentioned process stabilizers and dehydration agents to the lactide at a later stage, such as for instance prior to the flaking and/or after the flaking step. If the stabilizers are added to the lactide after flaking, the stabilizers may be sprayed or coated onto the lactide flakes.

We have further found that the presence of the above-mentioned process stabilizers and dehydration agents also increases the stability of the lactide particles during storage.

It is of course desired to have as little as possible material such as process stabilizers and dehydration agents present in the lactide particles other than lactide. Therefore, the lactide particle usually comprises more than 95% by weight lactide, preferably more than 98.5% by weight lactide, most preferably more than 99.5% by weight.

Depending on the lactide preparation and/or purification method the flaking process according to the present invention can either be combined with the preparation and/or purification, or not. For instance, if the lactide is obtained form distillation, it makes sense to directly couple a flaking machine to the distillation column because the lactide is already in its melted form. Also, if the final purification step of the lactide comprises melt-crystallization, a flaking machine can be directly coupled to the melt crystallisator.

The invention is further illustrated by means of the following non-limiting examples.

EXAMPLE 1

Flaking of L-Lactide Using a Lab-Scale Rotating Drum Flaker

Fresh L-lactide ex. Purac® (<5 meq/Kg free lactic acid) was molten using a stirred, oil-heated vessel. Subsequently, the liquid with a temperature of between 105-120° C. was metered during flaking into the dip pan underneath a rotating drum flaker having a surface area of 0.75 m$^2$. The liquid lactide was dosed at such a rate that the level of the liquid remained constant in the dip pan.

Due to the internal cooling of the drum, the lactide solidifies on the drum surface. The cooling water for the rotating drum was kept at a temperature between 10 and 35° C. and the rotational speed at between 5 and 15 rpm. Further, the dipping depth of the drum into the molten lactide was varied and tests were done at a dipping depth of 20 mm and 50 mm. The flakes produced have an average height of between 0.3 and 0.7 mm, a width of 1 to 3 mm and a length of 3 to 10 mm. The surface area per unit of volume varied between 4000 and 10000 m$^{-1}$. The bulk density was between 500 and 600 kg/m$^{-3}$.

The invention claimed is:
1. Method for the manufacture of stable lactide particles comprising:
directly contacting an entire amount of a single stream of a molten lactide composition with a solid surface having a temperature lower than the melting point of the lactide, allowing the entire amount of the single stream of the molten lactide composition to solidify on the solid surface, and removing the solid lactide as lactide particles from the solid surface, wherein the lactide particles have a surface area per unit of volume of from 1,000 to 10,000 m$^{-1}$.

2. Method according to claim 1, wherein the solid surface is cooled by external or internal means.

3. Method according to claim 1, wherein the removal is by contacting the solid surface with the solidified lactide with a scraping device.

4. Method according to claim 1, wherein said method is carried out with a drum flaker or belt flaker.

5. Method according to claim 1, wherein the obtained lactide particles are sieved.

6. Stable lactide particle obtainable by the method according to claim 1.

7. Method according to claim 1, wherein the lactide particles have a surface area per unit of volume of from 1,000 to 3,000 m$^{-1}$.

8. Method according to claim 1, wherein the stable lactide particles have a surface area per unit of volume of from 3,000 to 10,000 m$^{-1}$.

9. Stable lactide particle of claim 6, wherein the lactide particle comprises more than 95% by weight lactide.

10. Stable lactide particle according to claim 9, wherein the lactide present in the particle contains more than 95% by weight D-lactide.

11. Stable lactide particle according to claim 9, wherein the lactide present in the particle contains more than 95% by weight L-lactide.

12. Stable lactide particle of claim 6, wherein the water content is below 200 ppm.

13. Stable lactide particle of claim 6, wherein the free lactic acid content is below 50 milli-equivalents per kg lactide (meq·Kg$^{-1}$).

14. Method for the manufacture of stable lactide particles consisting of:

directly contacting an entire amount of a flow of a molten lactide composition with a solid surface having a temperature lower than the melting point of the lactide, allowing the entire amount of the flow of the molten lactide composition to solidify on the solid surface, and removing the solid lactide as lactide particles from the solid surface, wherein the lactide particles have a surface area per unit of volume of from 1,000 to 10,000 m$^{-1}$.

15. Method according to claim 14, wherein the flow of the molten lactide composition is a single stream.

* * * * *